United States Patent [19]
Nicolaus

[11] Patent Number: 5,279,836
[45] Date of Patent: Jan. 18, 1994

[54] TOPICAL USE OF CALCITONIN FOR THE PREPARATION OF MEDICATIONS IN SENILE IDIOPATHIC CATARACT AND A PHARMAEUTICAL COMPOSITION THEREOF

[75] Inventor: Bruno J. R. Nicolaus, Monza, Italy
[73] Assignee: Mediator S.R.L., Milan, Italy
[21] Appl. No.: 828,174
[22] Filed: Jan. 30, 1992

[30] Foreign Application Priority Data
Feb. 19, 1991 [IT] Italy ................... 421 A/91

[51] Int. Cl.⁵ .................. A61K 9/08; A61K 35/55
[52] U.S. Cl. ................... 424/484; 424/520; 424/562; 424/568; 514/808; 514/912
[58] Field of Search ............ 424/401; 514/912, 913, 514/914, 915, 808

[56] References Cited
U.S. PATENT DOCUMENTS

| | | | |
|---|---|---|---|
| 4,241,051 | 12/1980 | Chrishe | 514/808 |
| 4,994,439 | 2/1991 | Longenecker | 514/808 |
| 5,011,678 | 4/1991 | Wang | 514/808 |

OTHER PUBLICATIONS

"Endocrine regulation of calcium and phosphate in rat eye lens and its significance in cataract formation", Indian Journal of Experimental Biology; Srivastava et al., pp. 365–368 (Apr. 1990).
"Hormonal Regulation of Calcium in Rat Eye Lens", Indian Journal of Experimental Biology; Srivastava et al. pp. 345–346 (May 1987).

*Primary Examiner*—Thurman K. Page
*Assistant Examiner*—Sally Gardner
*Attorney, Agent, or Firm*—Oblon, Spivak, McClelland, Maier & Neustadt

[57] ABSTRACT

A new use of calcitonin, as an active principle, is provided for the preparation of topically appliable medications in the treatment of pre-senile and senile idiopathic cataract; and a pharmaceutical composition containing elcatonin as active principle for the preparation of a collyrium.

4 Claims, No Drawings

TOPICAL USE OF CALCITONIN FOR THE PREPARATION OF MEDICATIONS IN SENILE IDIOPATHIC CATARACT AND A PHARMAEUTICAL COMPOSITION THEREOF

DESCRIPTION

The present invention relates to the topical use of calcitonin in the therapy of pre-senile and senile idiopathic cataract; and a pharmaceutical composition thereof.

Senile cataract is one of the main causes of sight lowering in all countries and one of the major causes of blindness in developing countries. Senile cataract is connected with the age of the patient. There are indeed variations in the age of appearance of cataract and in its evolution, depending on the subjects and on geographical places. Among the main elements of risk there are: illumination, race, geographical factors, general health conditions (diabetes, glaucoma, arterial hypertension, lipids metabolism), nutrition, social factors. (B. Lumbroso et al., Records of the Congress: Cataratta ed Età-Rome, 25 Nov. 1989 -pages 27-39).

The exact etiopathogenesis of pre-senile and senile cataract is not known. Among the most accredited hypotheses there are described, in EP 0213091, three main mechanisms: the oxidation of the structural proteins with the formation of insoluble aggregates; the denaturization of the lens proteins or the alteration of the lens membrane permeability.

According to other authors, the cataract pathogenetic mechanism is referable to three groups of hypotheses: the epithelial, the capsular or the biochemical one.

According to the first hypothesis there is a relationship of cause and effect between an early alteration of the epithelium and a secondary alteration of the fibres.

The biochemical hypothesis explains the opacification of the lens with a metabolic alteration concerning the lenticular fibres, so that the lenticular proteins being soluble become insoluble by precipitation.

The capsular hypothesis attributes instead the opacification of the lens to an alteration of the capsular permeability which is reduced for the first and increases for the second.

In summary, one might nowadays affirm that two apparently different pathogenetic mechanisms correspond to the two clinical kinds of cataract, the nuclear and the cortical one.

An oxidation of the lenticular proteins occurs in the nuclear cataract, said proteins being soluble and gradually becoming insoluble, assuming an ambergris-like colour.

The fundamental alteration occurring in the cortical cataract is an altered equilibrium of sodium and potassium cations with an increase in sodium and calcium and a reduction in potassium. (L. Scullica, Records of the Congress "Cataratta", Symposium of Taormina, 1989).

It seems that sometimes the pre-senile and senile idiopathic cataract is accompanied by a massive oxidation of the -SH proteic and non proteic groups of the lens. (M. Testa et al., Exp. Eye Res. 1969, 8, 447–460).

The existence of a direct correlation between the oxidizing activity of the biological liquids (BLOA) and the pre-senile and senile cataract has been also stressed. (M. Testa et al., J. of Ocular Pharmacology 1986, 12, 251-266); G. Iuliano et al., Proceedings of 3rd Int. Congress of the Intern. Assoc. for Cataract Related Research, S. Margherita Ligure 1987).

Accordingly it has been postulated that the anticataract action of some anti-inflammatory agents (NSAID), such as Bendazac (INN) and Benzydamine (INN), is due to the formation of metabolites (e.g. benzilic alcohol) able to modify the redox potential of the lens.

The anti-cataract action would be therefore strictly connected with the reducing properties of the drug.

It has been also stated that the Ca/Phosphate ratio in the lens and its pathological fluctuations can play an important role in the formation of the cataract (V.K. Srivastava et al., Amn. Ophtalmol., 1989, 21 (4), 149-152).

The action of calcitonin on calcium levels has been studied in vitro in the sheep lens, finding out that calcitonin raises the calcium levels proportionally with the incubation times, according to a not yet explained mechanism. (V.K. Srivastava et al. Curr. Sci. 1988, 57 (6), 295-296).

The same authors showed that the parenteral administration of vitamin $D_2$ and pig calcitonin to rats causes hypercalcemia and hypocalcemia in the lens and in the plasma respectively.

Accordingly they have suggested the possibility to regulate the calcium levels with effective doses of vitamin $D_2$ and calcitonin, said levels being critical for the formation of the cataract. (V.K. Srivastava et al., Indian J. Exp. Biol. 1987, 25 (5), 345-346).

So far a pharmacotherapy resolutive of the pre-senile and senile idiopathic cataract does not exist and its final solution remains the surgical operation.

Awaiting this last step, symptomatic drugs having prevailingly an anti-inflammatory action are sometimes used, said drugs should have the property to slower the maturation of the cataract and the worsening of the visual acuity.

It is well known that the effectiveness level of these drugs is moderate. Thus, pharmacotherapy of cataract remains an unsolved problem.

In JP 61-178.928 there is provided the parenteral, rectal, intradermial or oral administration of natural calcitonins or aminosuberic analogues thereof as visual acuity regulators.

Calcitonin is a simple polypeptidic hormone made up of 32 amino acids. The amino acid sequence and their pattern in the calcitonin of the different animal species differ in a more or less remarkable way, although the physiological functions of said hormone remain substantially unchanged.

It seems that said functions regard the lowering of calcium ion and of inorganic phosphorus in blood, through an action on bones, on the intestinal apparatus, on kidneys, etc. Calcitonin is used in the treatment of the Paget disease, in osteoporoses, in hypercalcemiae and generally in all the diseases connected to an excess of calcium in blood, the diseases for which calcitonin is usually administered through parenteral or nasal way.

The ocular way could in theory be employed for the systemic administration of this polypeptide but it is not actually employed because of its low absorption due to the washing effect of the tears, to the enzymatic barriers and to the binding to the proteins of the tears and the ones of the corneal area; experimental data on the calcitonins absorption through ocular absorption are therefore not known (Lee et al., Int. J. Pharm. 1986, 29, 43-51;Lee et al , Pharm. Technol. 1987, 26-38).

In the present invention the term "calcitonin" means a calcitonin of natural origin such as the salmon, pig, eel or human one, and the semi- or total synthetic derivatives too with a similar structure and pharmacological activity; all these products are available on the market and widely described in scientific literature.

It has been now surprisingly found that using calcitonin topically an evident slowdown of the cataract maturation and a visual capacity relative stabilization without remarkable systemic effects can be obtained; retarding in this way the cataract resolution by surgical operation.

The object of the present invention is therefore the use of calcitonin, as active principle, in the preparations of medicaments for the therapeutic topical application of the presenile and senile idiopathic cataract.

The pharmaceutical compositions usable for the above described purpose, contain calcitonin as the active principle, in a dosage unit of 0.05 U.I. to 20 U.I.. The term "International unit" (U.I.) as used in the present invention corresponds to the definition established by the WHO in relation to the International Reference Preparations for the different calcitonins species (the human, pig, salmon and eel ones) biological assay distributed by the National Institute for Biological Standards and Control (NIB-SAC), South Miims, Potters bar, Hertfordshire, EN6 30G, United Kingdom.

Said pharmaceutical compositions contain calcitonin, as the active principle, and a pharmaceutically acceptable carrier useful for the preparation of a medicament for the topical application.

The pharmaceutical compositions for ocular administration of the present invention is carried out by suitable pharmaceutical forms such as, for instance, collyriums and ocular baths. The active principle used for the preparation of the collyrium must have a proper purity and the carrier consists of for instance, deionized, non-pyrogenic and sterile water.

Buffer mixture such as, for instance, citrates and phosphates; isotonic agents such as, for instance, sodium chloride; antioxidants such as, for instance, methyl or propyl p-hydroxy benzoate; wetting agents such as, for instance, quaternary ammonium salts and pentacyclic triterpenes can be added in the carriers; and agents modulating the penetration of the lenticular barrier if necessary.

In the preparation of the collyrium for the use described in the present invention, it is preferred in particular to use elcatonin in a dosage unit of from 0.05 to 20 U.I. which will be contained in a volume of 5–15 ml of a carrier consisting of deionized, a pyrogenic and sterile $H_2O$, with the addition of a buffer of citric acid and sodium citrate, preferably obtained by total—synthetic way, to obtain a pH from 5.0 to 7.0; surfactants such as ammonium, sodium or potassium glycyrrhizinate and benzalconium chloride; preserving agents such as methyl or propyl p-hydroxy benzoate; and modulators of the penetration of the lenticular barrier in a concentration from 0.1% to 0.5% (pv) of the total volume of the formulation. If desired, an impromptu collyrium can also be prepared, consisting of a pharmaceutically suitable carrier contained in a sealed ampoule and of an active principle, contained in a separate container in the form of a powder or of a small sterile tablet in such a way that calcitonin, as the active principle of said composition, is stable in time.

The above mentioned carrier could be made of deionized non-pyrogenic, sterile water with the addition of a buffer mixture of citric acid and sodium citrate, preferably obtained by totally synthetic way, to obtain a pH from 5.0 to 7.0; surfactants such as ammonium, sodium or potassium glycyrrhizinate and benzalconium chloride; preserving agents such as methyl or propyl p-hydroxy benzoate; and modulators of the penetration of the lenticular barrier in a concentration from 0.1% to 0.5% (pv) of the total volume of the formulation.

The pharmaceutical compositions described in the present invention, have the property to pass through the eye lenticular barrier and provide an effective therapeutical action in the presenile or senile idiopathic cataracts. Their activity has been evaluated through the pharmacological assay described hereinafter.

BIOAVAILABILITY OF THE COLLYRIUM IN THE AQUEOUS HUMOR AND IN THE SERUM

The intraocular absorption of the collyrium prepared as described hereinafter in Example 1, and topically administered to rabbits with whole corneas has been evaluated.

42 male rabbits of the New Zealand race having a weight of about 3 kg have been used.

After instillation of fluorescein at 2% and subsequent washing with physiological solution, the corneas of all the rabbits have been carefully examined before of the pharmacological treatment, with the aim to realize if there are alterations in the corneal epithelium that could have influenced the trans-corneal passage of the drug.

The collyrium is employed in a percent concentration of 5000 U.MRC.

The animals have been divided into two groups: 0.1 ml of collyrium corresponding to 5 U.MRC have been instilled in the right eye conjunctival sac of each rabbit of the first group, while 0.1 ml of placebo collyrium (only excipients) have been instilled in the right eye conjuctival sac of each rabbit of the second group.

The lower and the upper eyelids have been gently closed after the instillation of the collyrium in order to uniformly distribute the drug.

Upon washing of the cornea and of the conjunctive with physiological solution, in order to avoid infections of the sample, 0.2 ml of the aqueous humor of the anterior chamber were taken by Keratocentesis after surface anesthesia of the eyeball with 3% carbocain.

At the same time a blood sample from the ear marginal vein has been taken for the assay of the drug in serum.

The RIA method has been utilized for the elcatonin assay in serum and in aqueous humor.

The data obtained have been analyzed with the Student's t-test in order to verify the reliability of the comparison between the treatment and the placebo.

The concentrations of elcatonin in the aqueous humor of the treated rabbits appear to be high with scarce dispersion. The intraocular absorption of the drug is rapid, said drug being already present at high levels 1 hour after administration.

The plasma concentrations are by far lower, but they show the same tendency with a peak after the second hour.

No animal showed systemic phenomena of the drug intolerance nor local toxic phenomena, concerning in particular the corneal epithelium.

After the Keratocentesis a new test of the corneal surface integrity was performed with instillation of 2% fluorescein and washing with physiological solution.

It can be concluded that the topical administration of elcatonin is more suitable than the systemic one, because it allows to reach therapeutically effective concentrations in the aqueous humor and it does not involve systemic intolerance risks.

EXAMPLE 1

1600 μg of elcatonin (6500 U.I./mg activity) have been exactly weighed and dissolved at room temperature under a sterile nitrogen stream and stirring, in a carrier composed by 37 mg of citric acid and 63 mg of sodium dihydric citrate as buffering agents; 130 mg of methyl p-hydroxy benzoate and 20 mg of propyl p-hydroxy benzoate, as preserving agents; and H$_2$O to 100 ml.

The pH is adjusted to 6.0 with NaOH 1N.

EXAMPLE 2

The composition is prepared as provided in the Example 1, using 200 mg of acetic acid and 200 mg sodium trihydrate acetate (total synthetic quality) as buffering agents, the pH is fixed at 5.0 adding HCl 1N.

We claim:

1. A method for the treatment of pre-senile and senile idiopathic cataract of any eye, comprising:
   topically applying to said eye a therapeutically effective amount of a calcitonin sufficient to alleviate pre-senile or senile idiopathic cataract within said eye.

2. The method of claim 1, wherein 0.05 to 20 I.U. of said calcitonin is topically applied.

3. The method of claim 1, wherein said calcitonin is elcatonin.

4. The method of claim 1, wherein said calcitonin is applied in the form of a collyrium.

* * * * *

UNITED STATES PATENT AND TRADEMARK OFFICE
CERTIFICATE OF CORRECTION

PATENT NO. : 5,279,836
DATED : January 18, 1994
INVENTOR(S) : Bruno J. R. Nicolaus It is certified that error appears in the above-indentified patent and that said Letters Patent is hereby corrected as shown below:

On the title page, Item [30], Column 1, line 5

The Foreign Application Priority number should read:

--MI 91 A000421--

On the title page, Item [54], Column 1, line 5
The Title should read: --TOPICAL USE OF CALCITONIN FOR THE

PREPARATION OF MEDICATIONS IN SENILE IDIOPATHIC CATARACT

AND A PHARMACEUTICAL COMPOSITION THEREOF--

Signed and Sealed this

Twelfth Day of July, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,279,836
DATED : January 18, 1994
INVENTOR(S) : Bruno J. R. NICOLAUS It is certified that error appears in the above-indentified patent and that said Letters Patent is hereby corrected as shown below:

On the Title Page, Item [30], the Foreign Application Priority number should read:

--MI 91 A000421--

On the Title Page, Item [54], and column 1, line 5, the title should read:

--TOPICAL USE OF CALCITONIN FOR THE PREPARATION OF MEDICATIONS IN SENILE IDIOPATHIC CATARACT AND A PHARMACEUTICAL COMPOSITION THEREOF--

This certificate supersedes Certificate of Correction issued July 12, 1994.

Signed and Sealed this

Sixth Day of December, 1994

Attest:

BRUCE LEHMAN

*Attesting Officer*     *Commissioner of Patents and Trademarks*